(12) United States Patent
Takaoka

(10) Patent No.: US 7,804,067 B2
(45) Date of Patent: Sep. 28, 2010

(54) METHOD OF OBSERVING AND METHOD OF WORKING DIAMOND STYLUS FOR WORKING OF ATOMIC FORCE MICROSCOPE

(75) Inventor: Osamu Takaoka, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 508 days.

(21) Appl. No.: 11/951,768

(22) Filed: Dec. 6, 2007

(65) Prior Publication Data

US 2008/0141764 A1 Jun. 19, 2008

(30) Foreign Application Priority Data

Dec. 8, 2006 (JP) ............... 2006-332085

(51) Int. Cl.
*G01Q 80/00* (2010.01)
*G01Q 40/00* (2010.01)
*G01Q 60/04* (2010.01)
*G01Q 60/02* (2010.01)

(52) U.S. Cl. ............... 250/307; 850/19; 850/22; 850/23; 850/62

(58) Field of Classification Search ............... 250/307, 250/311; 850/19, 22–23, 60, 62
See application file for complete search history.

(56) References Cited

U.S. PATENT DOCUMENTS 5,936,237 A * 8/1999 van der Weide ............. 250/234
5,989,511 A * 11/1999 Gruen et al. ................ 423/446
2008/0191372 A1 * 8/2008 Takaoka ...................... 264/39

OTHER PUBLICATIONS

Edinger et al., "Electron-Beam-Based Photomask Repair", J. Vac. Sci. Technol. B, vol. 22, No. 6, pp. 2902-2906 (2004).
Morikawa et al., "Defect Repair Performance Using the Nanomachining Repair Technique" Proc. of SPIE vol. 5130 pp. 520-527 (2003).
Liukkonen, "Contact Angle of Water on Paper Components: Sessile Drops versus Environmental Scanning Electron Microscope Measurements", Scanning vol. 19, pp. 411-415 (1997).
Taniguchi et al., "Electron Beam Assisted Chemical Etching of Single Crystal Diamond Substrates", Jpn. J. Appl. Phys. vol. 35, pp. 6574-6578 (1996).
Taniguchi et al., "Electron Beam Assisted Chemical Etching of Single-Crystal Diamond Substrates with Hydrogen Gas", Jpn. J. Appl. Phys. vol. 36, pp. 7691-7695 (1997).

* cited by examiner

*Primary Examiner*—Thomas P Noland
(74) *Attorney, Agent, or Firm*—Brinks Hofer Gilson & Lione

(57) ABSTRACT

When a characterization of a tip of a diamond stylus for working is needed, the tip of the diamond stylus for working used is observed by a high resolution scanning electron microscope of a high acceleration voltage under a steam atmosphere. When the tip of the diamond stylus for working is worn or when a shape of the tip of the stylus needs to be changed, the tip of the diamond stylus for working is worked by selectively irradiating an electron beam only to a necessary region by increasing an amount of steam and an amount of a current of the electron beam. When a working chip is strongly adhered to the diamond stylus for working and needs to be removed, the electron beam is selectively irradiated only to the working chip adhered to the tip of the diamond stylus for working to be removed under a xenon fluoride atmosphere.

4 Claims, 3 Drawing Sheets

METHOD OF OBSERVING AND METHOD OF WORKING DIAMOND STYLUS FOR WORKING OF ATOMIC FORCE MICROSCOPE

RELATED APPLICATIONS

This application claims priority under 35 U.S.C. §119 to Japanese Patent Application No. JP2006-332085 filed Dec. 8, 2006, the entire content of which is hereby incorporated by reference.

BACKGROUND OF THE INVENTION

The present invention relates to a characterization (here, a characterization signifies to evaluate whether a shape for achieving a desired function is constituted) of a tip of a diamond stylus for working of an apparatus compounded with an atomic force microscope and a scanning electron microscope and additional working of a diamond stylus and removal of a working chip adhered to the stylus.

In accordance with progress of miniaturization of a semiconductor integrated circuit, also a pattern on a photo mask constituting an original blank of transcribing the pattern has been progressed. A photo mask is an original blank, and therefore, when there is a defect, the defect is fabricated in all of objects to be transcribed, and therefore, the photo mask is requested to be free of a defect. The defect is inevitably brought about in view of a mask working process, and therefore, the defect is corrected by using a laser. However, when the pattern is miniaturized, also the defect to be corrected becomes small, the laser cannot deal with such a small defect, and therefore, in recent times, a correction using a focused ion beam (FIB) has been used as a standard. An opaque defect and a clear defect are corrected by a gas-assisted etching of FIB or an FIB-CVD light shielding film. Also an FIB defect correcting apparatus reaches a limit because in accordance with the progress of the miniaturization, an allowable range of an image resolution or a reduction in a transmittance by gallium injection by short wavelength formation of a reduction projection exposure apparatus becomes severe and a technology of overcoming the limit has been requested. In order to avoid the reduction in the transmittance by higher resolution formation and gallium injection derived from FIB, a defect correction apparatus (K. Edinger, H. Becht, J. Bihr, V. Boegli, M. Budach, T. Hofmann, H. P. Coops, P. Kuschnerus, J. Oster, P. Spies and B. Weyrauch, J. Vac. Sci. Technol. B22 2902-2906 (2004)) using an electron beam, or a technology of physically removing an opaque defect by a stylus harder than a material to be worked (defect) (scratching) by using an atomic force microscope (AFM) has been reduced into practice (Y. Morikawa, H. Kokubo, M. Nishiguchi, N. Hayashi, R. White, R. Bozak, and L. Terrill, Proc. of SPIE 5130 520-527 (2003)). Although a clear defect can easily be corrected by a defect correcting apparatus using an electron beam, there is present a case in which an opaque defect is difficult to be corrected practically. On the other hand, in a physical removing apparatus using an atomic force microscope, although an opaque defect can be corrected, a clear defect cannot be corrected in view of a principle thereof.

A physical removing apparatus using an atomic force microscope uses one obtained by sharpening diamond as a working stylus. Even a removing capability of diamond is reduced owing to a wear of a stylus or a working chip adhered to the stylus in correcting to remove an opaque defect. A characterization of a tip of a working stylus becomes important in excellently removing an opaque defect with a reproducibility. According to an apparatus compounded with a defect correcting apparatus using an electron beam and a physical defect removing apparatus using an atomic force microscope, also an in-situ characterization of a front end of a working stylus by an electron beam can be carried out in view of a principle thereof.

According to a working apparatus compounded with an atomic force microscope and a scanning electron microscope, when a sharpened tip of a stylus is observed by the scanning electron microscope, since a conductivity of diamond constituting a material of the stylus is deficient, observation is carried out normally by an acceleration voltage equal to or lower than 2 kV such that charge up is not brought about. However, high resolution observation is difficult by such an acceleration voltage so far as a working distance is shortened, and a special stylus attaching jig needs to be prepared. Further, in a case of shortening the working distance, when detection is carried out by a secondary electron detector normally provided upward from an object lens, a charged-up image is liable to be brought about, in order to avoid charge up, the acceleration voltage needs to be further lowered, and it is difficult to achieve a high resolution image under a condition without charge up. Although charge up is alleviated when the detector is provided downward from the object lens, only an image having a low S/N is achieved when the working distance is short. Further, when a defect correcting apparatus using an electron beam and a physical removing apparatus using AFM are compounded, there poses a problem that a restriction in a position of the secondary electron detector or the working distance is severe and it is also difficult to apply a background art observing method.

In recent times, there has been developed a scanning microscope technology of an environment control type capable of carrying out high resolution observation even under low vacuum of 100 through 1000 Pa, by irradiating an electron beam while making water or nitrogen flow at inside of a vacuum chamber, even high resolution observation of an insulating substance of a ceramic or a living body sample is made to be able to be carried out by a high acceleration voltage without charge up (for example, Nonpatent A. Liukkonen, Scanning 19 411(1997)).

Further, an electron beam can carry out etching by a chemical effect by selecting an assist etching gas. It is known that diamond can be worked by irradiating the electron beam under a hydrogen or oxygen atmosphere (J. Taniguchi, I. Miyamamoto, N. Ohno, and S. Honda, Jpn. J. Appl. Phys. 35 6574-6578 (1996) and J. Taniguchi, I. Miyamamoto, N. Ohno, K. Kanatani, M. Komuro and S. Honda, Jpn. J. Appl. Phys. 36 7691-7695 (1997)). Even under a steam atmosphere, a removing effect similar to that of hydrogen or oxygen can be expected. Further, it is known that even Cr or MoSi or glass can be removed by irradiating the electron beam under an atmosphere of xenon fluoride.

It is a problem of the invention that in an apparatus compounded with a defect correcting apparatus using an electron beam and a physical defect removing apparatus using an atomic force microscope which can perform a clear defect correction and an opaque defect correction in the same apparatus, by utilizing the above-described characteristic of the electron beam in observation and working, a diamond stylus for working of an atomic force microscope is observed with high resolution, when the stylus is deteriorated or adhered with working chip, a damage on the diamond stylus is reduced, the diamond stylus is worked to be sharpened, or a dirt is removed therefrom.

SUMMARY OF THE INVENTION

In order to resolve the above-described problem, a method of observing a diamond stylus for working of an atomic force microscope according to the invention is characterized in that in a working apparatus compounded with an atomic force microscope and a scanning electron microscope, a tip of a diamond stylus for working of the atomic force microscope is observed by irradiating an electron beam of an acceleration voltage of 10 through 30 kV by the scanning electron microscope under a steam atmosphere.

Further, it is characterized that a diamond stylus for working is observed by the method of observing a diamond stylus for working of an atomic force microscope, thereafter, a tip of the diamond stylus for working is worked into a desired shape by increasing an amount of the steam and an amount of a current of the electron beam.

Further, it is characterized that when the diamond stylus for working is observed by the method of observing a diamond stylus for working of an atomic force microscope, in a case in which it is determined that a tip of the diamond stylus for working is worn, the worn tip of the diamond stylus for working is resharpened by increasing an amount of the steam and an amount of a current of the electron beam.

Further, it is characterized that, when the diamond stylus for working is observed by the method of observing the diamond stylus for working of an atomic force microscope, in a case in which it is determined that a working chip is adhered to a diamond stylus, an electron beam is irradiated to the working chip adhered to a tip of the diamond stylus for working to be removed under a xenon fluoride atmosphere.

Charge up is alleviated by ionizing steam by the electron beam, and the tip of the diamond stylus can be observed without reducing a resolution by the charge up. Although a primary beam is scattered by steam and the resolution is reduced, the reduction can be avoided by increasing the acceleration voltage and high resolution observation can be carried out.

Etching can be carried out by oxidizing diamond by increasing the amount of steam and the amount of the current of the electron beam. The diamond stylus can be worked into a desired shape by selectively irradiating a desired position. Further, with regard to the worn diamond stylus, tip thereof can be resharpened. Also when a high aspect shape is needed and the like, the tip can be worked into a desired shape.

Xenon fluoride gas-assisted etching by the electron beam can remove only MoSi or Cr of a material to be worked constituting a working chip adhered to a tip of the stylus without damaging the diamond stylus.

Observation through working of the diamond stylus are carried out by the electron beam, and therefore, the high resolution observation can be carried out as described above, and therefore, highly accurate working can be carried out, further, less damaging working can be carried out simply and conveniently.

DETAILED DESCRIPTION OF THE PREFERRED EMBODIMENT

An embodiment of the invention will be explained in details in reference to the drawings as follows.

A mask having a defect is introduced into an apparatus including a gas introducing system and compounded with a scanning electron microscope capable of correcting the defect by using an electron beam and an atomic force microscope capable of removing the defect physically by a scanning stylus. An opaque defect is removed to be corrected by physically removing an extraneous portion by the atomic force microscope having a stylus comprising, for example, diamond harder than a material to be worked (Cr or MoSi) and a hard cantilever which is difficult to be twisted, and a clear defect is corrected by piling up a light shielding film by a necessary height by an electron beam CVD by selectively irradiating an electron beam only to a defect region under an environment of a gas of a carbon containing substance of naphthalene, phenanthrene or the like.

According to the working stylus for removing the opaque defect, an imaging resolution or a removing capability thereof is reduced by wear or adhering a working chip in being used. In such a case, a characterization of a tip of a working stylus is needed in order to determine whether the stylus is to be interchanged and in order to be informed of a cause of a reduction in the capability.

Figure 1A:
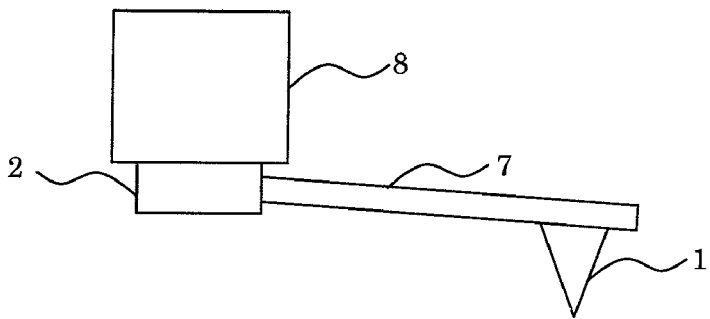
FIGS. 1A and 1B illustrate outline sectional views for explaining a case of carrying out a characterization of a tip of a diamond stylus for working according to the invention.
Figure 1B:
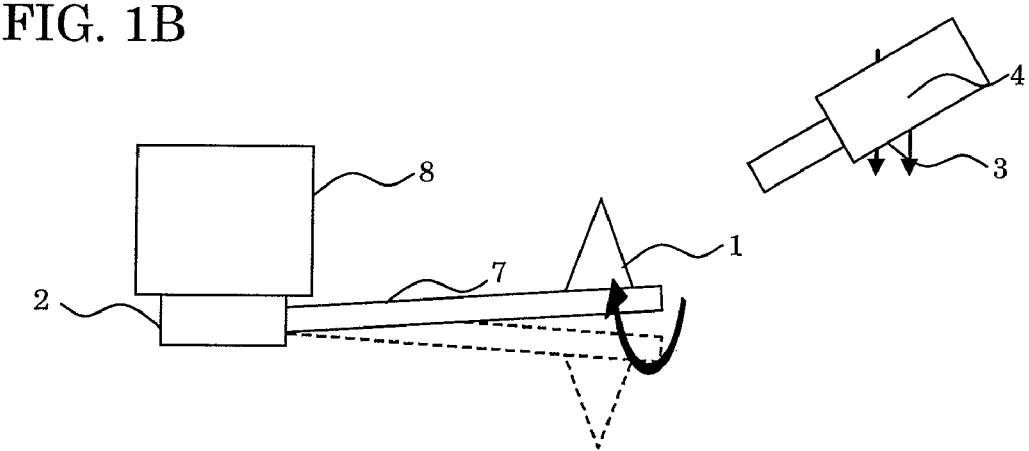

FIGS. 1A and 1B show an outline sectional view for explaining a case of carrying out a characterization of a tip of a diamond stylus for working according to the invention. As shown by FIGS. 1A and 1B, according to a characterization of a tip of a working stylus, first, by driving a piezo scanner 8, a diamond stylus 1 for working of an atomic force microscope is moved in XY directions to be moved to a position capable of irradiating an electron beam 4, thereafter, the diamond stylus 1 for working is inverted by 180° by a stylus rotating mechanism 2 by way of a cantilever 7 to be directed in a direction of impinging the electron beam 4.

Under the state, steam of 100 through 1000 Pa is introduced from a gas introducing system 3 into a vacuum chamber. A sharpness of the diamond stylus 1 for working is evaluated to determine by observing the diamond stylus 1 for working by a high resolution scanning electron microscope by irradiating an electron beam to a tip of the diamond stylus 1 for working of the atomic force microscope by a high acceleration voltage of 10 through 30 kV under a steam atmosphere. By neutralizing an electric charge generated by steam ionized by the electron beam 4, charge up can be prevented and observation can be carried out without reducing a resolution. By using the electron microscope by the high acceleration voltage, the electron beam can be narrowed and the electron beam can be restrained from being widened by scattering the electron beam by steam.

Figure 2A:
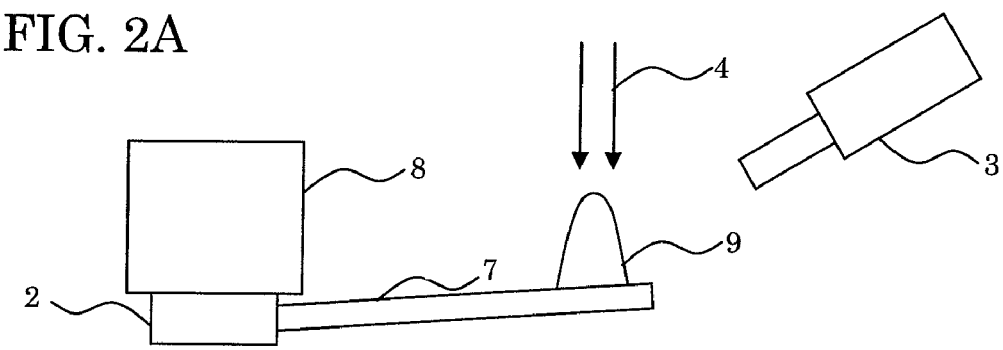
FIGS. 2A and 2B illustrate outline sectional views for explaining a case of resharpening a worn tip of a diamond stylus for working according to the invention.
Figure 2B:
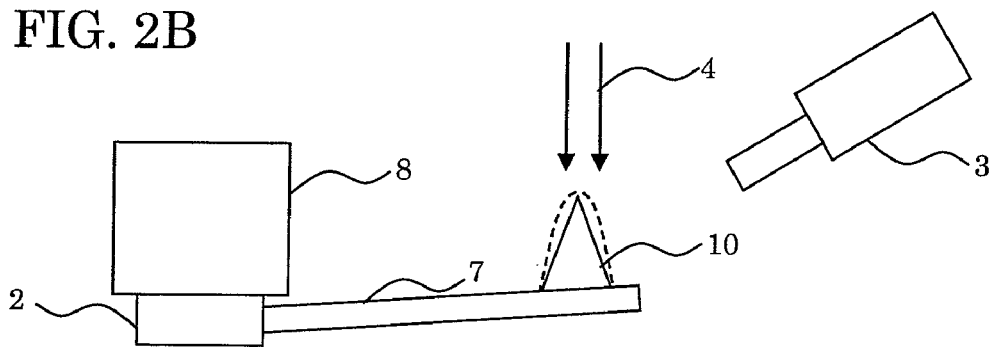

FIGS. 2A and 2B illustrate outline sectional views for explaining a case of resharpening a worn tip of a diamond stylus for working according to the invention.

When a working stylus is worn, in order to improve a removing capability or an imaging resolution, it is necessary to resharpen a working stylus. When it is necessary to work the tip of the stylus, as shown by FIGS. 2A and 2B, similar to the case of the characterization, the diamond stylus 1 for working is moved to a position capable of irradiating the electron beam 4, thereafter, the diamond stylus 1 is inverted by 180° by the stylus rotating mechanism 2 to be directed in the direction of impinging the electron beam 4. A high resolution observation is carried out under a steam atmosphere of 100 through 1000 Pa, a region to be worked for resharpening is determined, thereafter, an amount of steam and an amount of a current of the electron beam are increased more than those in the case of observation to selectively irradiate the electron beam 4 only to a necessary region, and the tip of the diamond stylus 1 for working of the atomic force microscope is resharpened by electron beam gas-assisted etching.

Figure 3A:
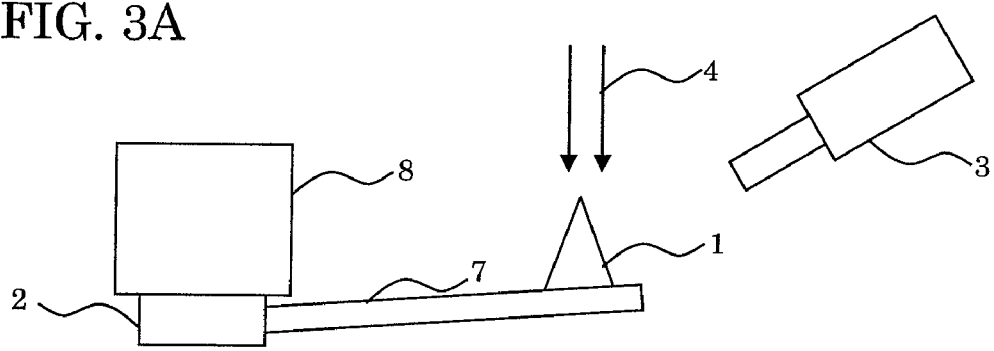
FIGS. 3A and 3B illustrate outline sectional views for explaining a case of changing a shape of a tip of a diamond stylus for working into a desired shape according to the invention.
Figure 3B:
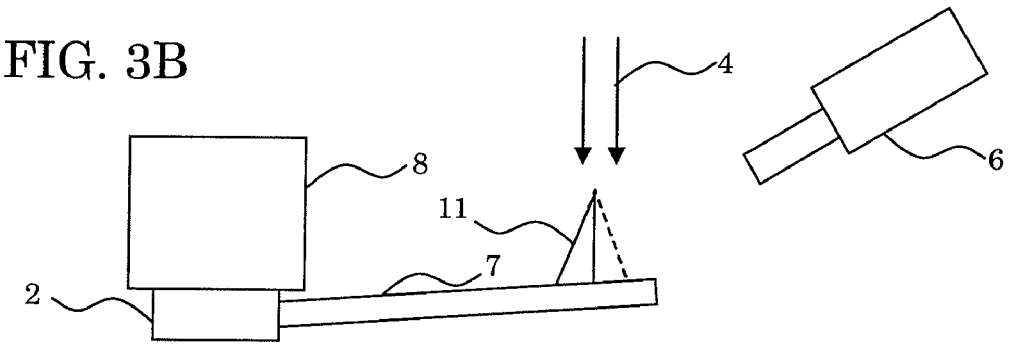

FIGS. 3A and 3B illustrate outline sectional views for explaining a case of changing a shape of a front end of a diamond stylus for working into a desired shape by working according to the invention.

In order to work a section nearly vertically or work a desired region by a shape of a blade having a high aspect ratio, a shape of a stylus needs to be changed. As shown by FIGS. 3A and 3B, also in this case, the diamond stylus 1 for working is moved to a position of capable of irradiating the electron beam 4, thereafter, the diamond stylus 1 is inverted by 180° by the stylus rotating mechanism 2 to direct in the direction of impinging the electron beam 4. High resolution observation is carried out under a steam atmosphere of 100 through 1000 Pa, a region to be worked is determined, thereafter, the electron beam is selectively irradiated only to a necessary region by increasing an amount of steam and an amount of a current of the electron beam more than those in the case of observation, and by electron beam gas-assisted etching, the tip of the diamond stylus 1 for working of the atomic force microscope is worked into a desired shape, for example, a face on a side of a tip of the cantilever of the diamond stylus 1 is worked into a vertical blade shape, or a blade shape having a high aspect ratio.

Figure 4A:
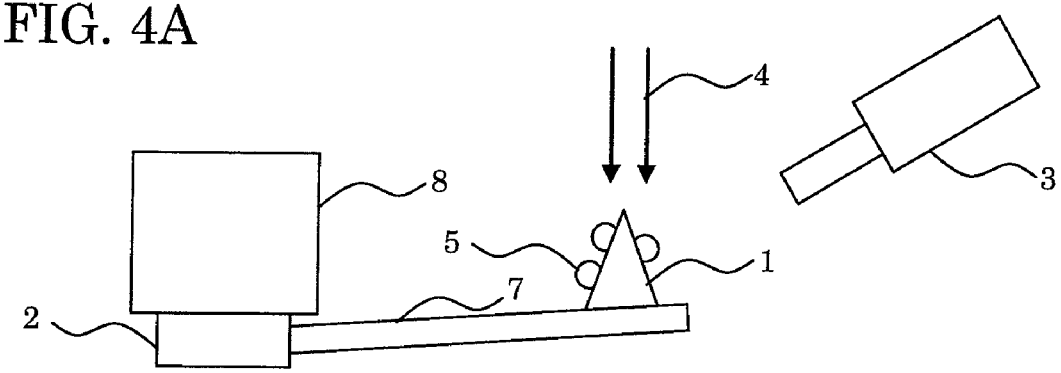
FIGS. 4A and 4B illustrate outline sectional views for explaining a case of removing a working chip adhered to a tip of a diamond stylus for working according to the invention.
Figure 4B:
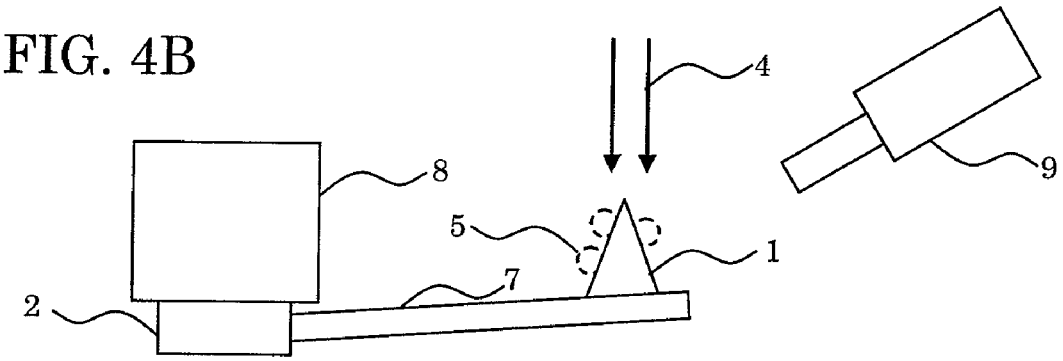

FIGS. 4A and 4B illustrate outline sectional views for explaining a case of removing a working chip adhered to a tip of a diamond stylus for working according to the invention.

When MoSi or Cr constituting a material to be worked is strongly adhered to a working stylus as a working chip and a removing capability or an imaging resolution is not excellent, it is necessary to remove the working chip adhered to the stylus. As shown in FIGS. 4A and 4B, also in this case, the diamond stylus 1 for working is moved to a position of capable of irradiating the electron beam 4, thereafter, the diamond stylus 1 is inverted by 180° by the stylus rotating mechanism 2 to be directed in a direction of impinging the electron beam 4. High resolution observation is carried out under a steam atmosphere of 100 through 1000 Pa, a region of removing a working chip 5 is determined, thereafter, steam is purged, the gas introducing system is switched to a xenon fluoride gas introducing system 6, and the electron beam 4 is selectively irradiated only to the working chip 5 adhered to the tip of the diamond stylus 1 for working of the atomic force microscope under the xenon fluoride atmosphere to remove the working chip. When there are a plurality of working chips, the respective working chips are removed by selectively irradiating the electron beam 4.

What is claimed is:

1. A method of observing a diamond stylus for working of an atomic force microscope characterized in that in a working apparatus compounded with an atomic force microscope and a scanning electron microscope, a tip of a diamond stylus for working of the atomic force microscope is observed by irradiating an electron beam of an acceleration voltage of 10 through 30 kV by the scanning electron microscope under a steam atmosphere.

2. A method of working a diamond stylus for working of an atomic force microscope characterized in that a diamond stylus for working is observed by the method of observing a diamond stylus for working of an atomic force microscope according to claim 1, thereafter, a tip of the diamond stylus for working is worked into a desired shape by increasing an amount of the steam and an amount of a current of the electron beam.

3. A method of working a diamond stylus for working of an atomic force microscope characterized in that when the diamond stylus for working is observed by the method of observing a diamond stylus for working of an atomic force microscope according to claim 1, in a case in which it is determined that a tip of the diamond stylus for working is worn, the worn tip of the diamond stylus for working is resharpened by increasing an amount of the steam and an amount of a current of the electron beam.

4. A method of working a diamond stylus for working of an atomic force microscope characterized in that when the diamond stylus is observed by the method of observing the diamond stylus for working of an atomic force microscope according to claim 1, in a case in which it is determined that a working chip is adhered to a diamond stylus, an electron beam is irradiated to the working chip adhered to a tip of the diamond stylus for working to be removed under a xenon fluoride atmosphere.

* * * * *